(12) United States Patent
Bernardino et al.

(10) Patent No.: US 10,758,391 B2
(45) Date of Patent: Sep. 1, 2020

(54) FINGER SLEEVE

(71) Applicants: Neal Bernardino, Newbury Park, CA (US); Eddie Yang, Woodland Hills, CA (US)

(72) Inventors: Neal Bernardino, Newbury Park, CA (US); Eddie Yang, Woodland Hills, CA (US)

( * ) Notice: Subject to any disclaimer, the term of this patent is extended or adjusted under 35 U.S.C. 154(b) by 439 days.

(21) Appl. No.: 15/098,046

(22) Filed: Apr. 13, 2016

(65) Prior Publication Data

US 2017/0296371 A1    Oct. 19, 2017

(51) Int. Cl.
| | | |
|---|---|---|
| *A61F 5/058* | (2006.01) | |
| *A61F 5/10* | (2006.01) | |
| *A61F 5/01* | (2006.01) | |
| *A63B 71/14* | (2006.01) | |

(52) U.S. Cl.
CPC ........ *A61F 5/0118* (2013.01); *A61F 5/05875* (2013.01); *A61F 5/05883* (2013.01); *A61F 5/10* (2013.01); *A63B 71/14* (2013.01)

(58) Field of Classification Search
CPC .... A61F 5/0118; A61F 5/013; A61F 5/05866; A61F 5/05875; A61F 5/10; A61F 2005/0181; A63B 71/14
USPC ........................ 602/22, 30, 60–63; 2/21, 163
See application file for complete search history.

(56) References Cited

U.S. PATENT DOCUMENTS

| | | | |
|---|---|---|---|
| 5,095,897 A * | 3/1992 | Clark ................. | A61F 5/05875 128/883 |
| 7,314,457 B2 * | 1/2008 | Reaux ................ | A61F 13/04 602/6 |
| 7,314,459 B2 * | 1/2008 | Bennett ............... | A61F 5/0118 602/20 |
| 8,211,044 B2 * | 7/2012 | Liebowitz ............ | A61F 5/10 602/22 |
| 8,539,614 B2 * | 9/2013 | Cote .................. | A41D 13/087 2/161.1 |
| 2013/0190671 A1 * | 7/2013 | Pastore .............. | A61F 5/10 602/22 |

\* cited by examiner

*Primary Examiner* — Keri J Nelson
(74) *Attorney, Agent, or Firm* — Mahesh Law Group, PC

(57) ABSTRACT

Disclosed herein is a finger sleeve support apparatus configured to restrain relative movement between two fingers on the hand of a wearer such that protection is afforded to the restrained fingers in certain types of activities.

17 Claims, 3 Drawing Sheets

FINGER SLEEVE

FIELD OF THE INVENTION

The present invention relates generally to a finger support mechanism, and more particularly, to a finger sleeve apparatus configured for restraining the relative movement between selective fingers of a wearer's hand such that protection is afforded to the restrained fingers without interfering with normal functions of the wear's hand.

BACKGROUND

In certain common activities, a person may incur injury to his hand or certain fingers of his hand because all the fingers are free to move independently of one another. For instance, when a weight trainer tries to rapidly grab a dumb bell or switch from a bar bell to free weights, one or more of his fingers may get hurt accidently due to a quick change in his hand motion or gesture. Placing a glove over the hand is one method of avoiding such injuries, but use of a glove may interfere with the person's manual ability. Alternatively, many grapplers use tape to attach their fingers together for support, but this method is only temporary and sometimes difficult to remove.

Therefore, a need exists for a restrictive support for use on selective fingers of a hand that does not interfere with normal functions of the hand.

SUMMARY OF THE INVENTION

The presently disclosed embodiments are directed to solving issues relating to one or more of the problems presented in the prior art, as well as providing additional features that will become readily apparent by reference to the following detailed description when taken in conjunction with the accompanying drawings.

One embodiment is directed to a finger sleeve support apparatus comprising: a cylindrical member comprising a protruding tab on a second end and a hem overlay on a first end, wherein a row of stitching is formed in the center of the cylindrical member to form a first finger sleeve having a first opening and a second finger sleeve having a second opening, wherein the first and second openings are configured to accommodate two fingers of a wearer's hand and restrain movement of the fingers.

In another embodiment, a finger sleeve support apparatus comprises a first cylindrical member having a first opening; a second cylindrical member connected to the first cylindrical member via a line of stitching, the second cylindrical member having a second opening; a protruding member disposed at a second end of the first and second cylindrical members; and a hem overlay disposed at a first end of the first and second cylindrical members, wherein the first and second cylindrical members are configured to allow two fingers of a user's hand to go through the openings and restrain relative movement of the two fingers Further features and advantages of the present disclosure, as well as the structure and operation of various embodiments of the present disclosure, are described in detail below with reference to the accompanying drawings.

BRIEF DESCRIPTION OF THE DRAWINGS

The present disclosure, in accordance with one or more various embodiments, is described in detail with reference to the following figures. The drawings are provided for purposes of illustration only and merely depict exemplary embodiments of the disclosure. These drawings are provided to facilitate the reader's understanding of the disclosure and should not be considered limiting of the breadth, scope, or applicability of the disclosure. It should be noted that for clarity and ease of illustration these drawings are not necessarily made to scale.

DETAILED DESCRIPTION OF EXEMPLARY EMBODIMENTS

Figure 1:
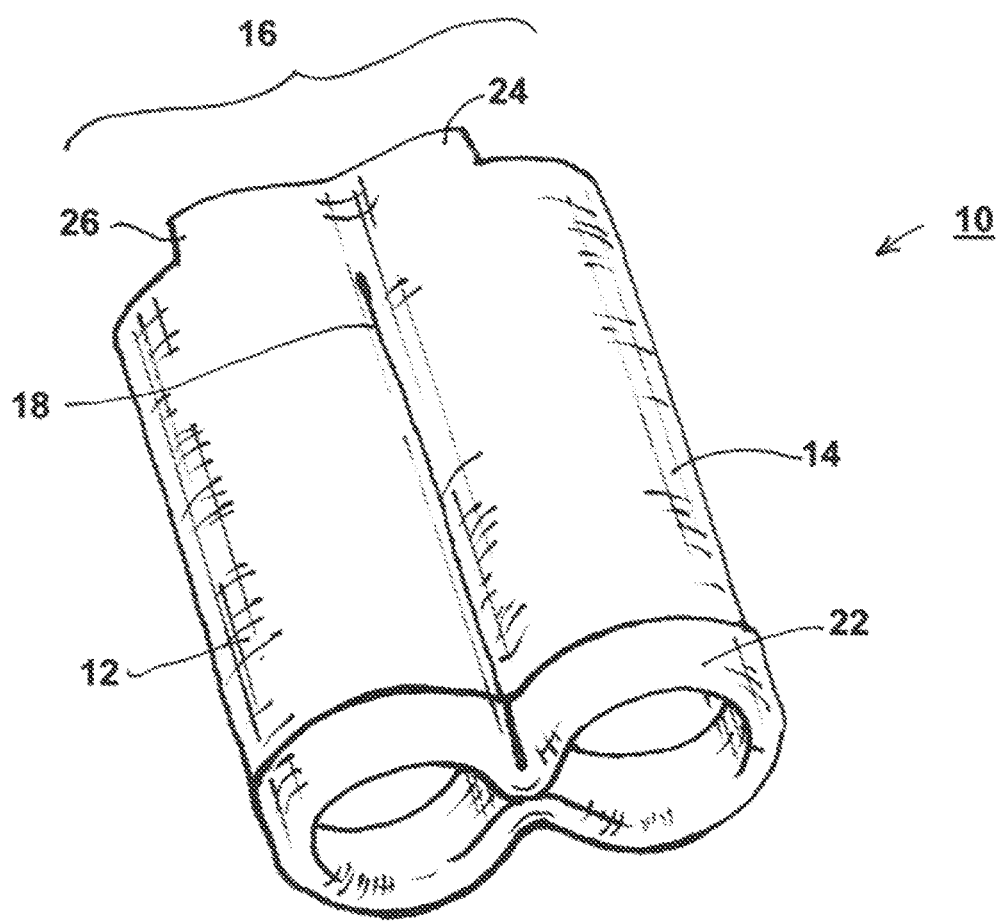
FIG. 1 is an isometric diagrammatical illustration of a finger sleeve apparatus in accordance with embodiments of the present invention.

The following description is presented to enable a person of ordinary skill in the art to make and use the invention. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the invention. Thus, embodiments of the present invention are not intended to be limited to the examples described herein and shown, but is to be accorded the scope consistent with the claims.

Reference will now be made in detail to aspects of the subject technology, examples of which are illustrated in the accompanying drawings, wherein like reference numerals refer to like elements throughout.

Figure 6:
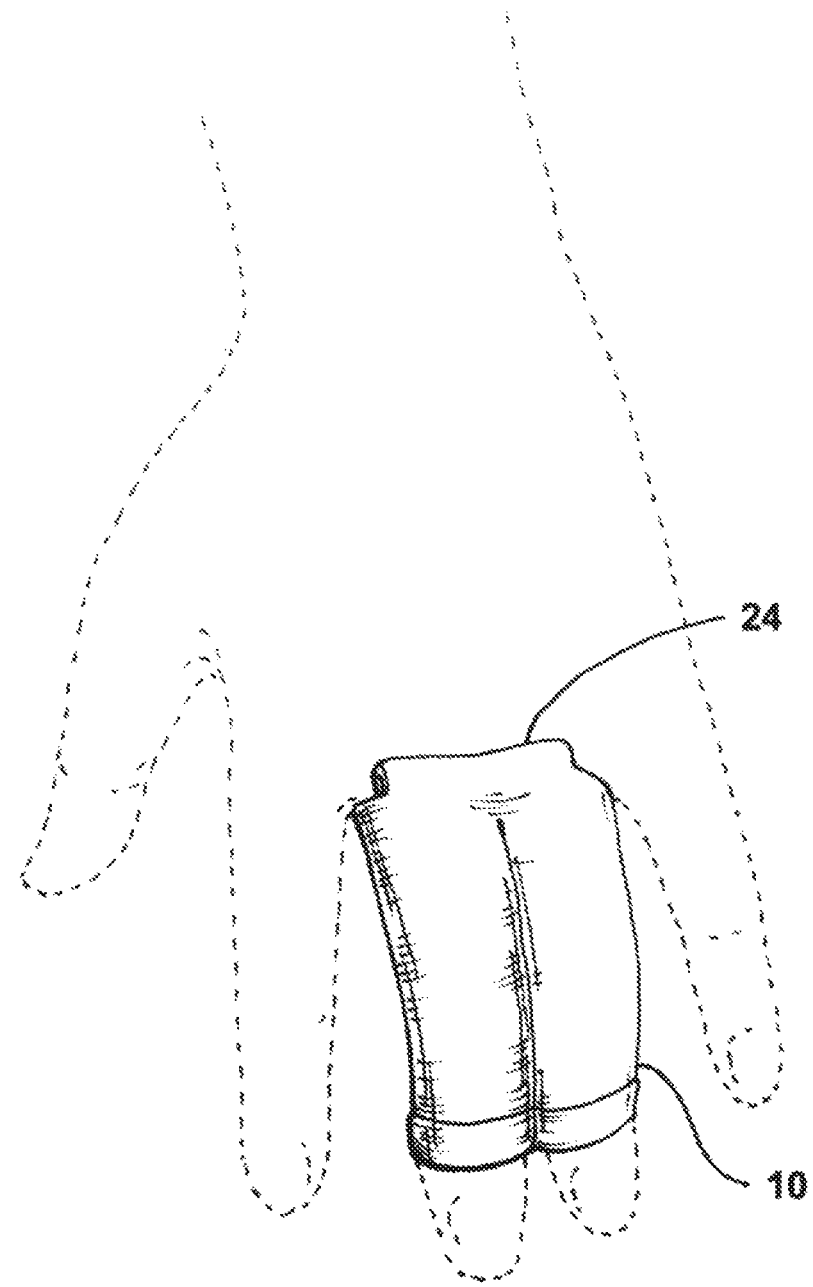
FIG. 6 is an isometric diagrammatical illustration of the finger sleeve apparatus of FIG. 1 as can be worn on a user's hand.

Referring now to FIG. 1, there is shown a finger sleeve apparatus 10 for supporting selective fingers of a hand, which comprises a first finger sleeve 12 and a second finger sleeve 14 in accordance with one embodiment of the present invention. The first finger sleeve 12 and the second finger sleeve 14 are sized and shaped so as to comfortably accommodate two fingers of a wearer's hand, as shown in FIG. 6 below.

The finger sleeve support apparatus 10 may be constructed from a generally cylindrical fabric component 16 having a hem overlay 22 at a first end of the finger sleeve support apparatus 10. In an exemplary embodiment, the fabric of the finger sleeve support apparatus 10 may comprise a moderate thickness of a spandex fabric, neoprene fabric, or other similar material. The hem overlay 22 may comprise a wear-resistant fabric.

The finger sleeve support apparatus 10 includes a first protruding tab 24 and an optional second protruding tab 26, both tabs 24, 26 disposed at a second end of the finger sleeve support 10. The two finger sleeves 12, 14 are formed in the cylindrical fabric component 16 by the addition of a substantially straight row of stitching 18 that extends from the hem overlay 22 and terminates proximate the tab 24. As can be seen in the illustration, the row of stitching 18 does not extend into the tabs 24, 26.

Figure 2:
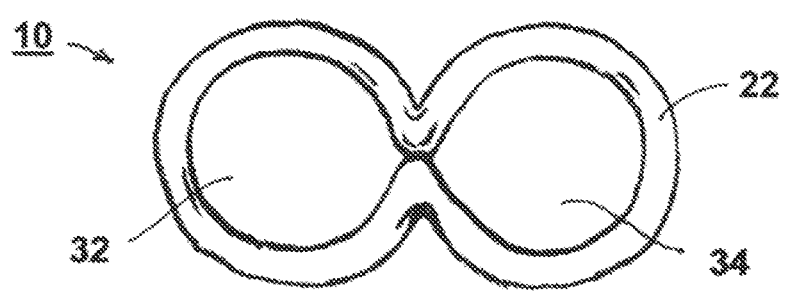
FIG. 2 is a first end view of the finger sleeve apparatus of FIG. 1 in accordance with embodiments of the present invention.

The row of stitching 18 holds together two diametrically opposed sides of the generally cylindrical fabric component 16 so as to form a first end cross section in the shape of a "figure eight," as best shown in FIG. 2. A first opening 32 in the finger sleeve support apparatus 10 is used for the insertion of a first finger from the second end of the finger sleeve support apparatus 10, and a second opening 34 in the finger sleeve support apparatus 10 is used for the insertion of a second finger. As can be appreciated by one skilled in the art, the hem overlay 22 functions to keep the first end of the finger sleeve support apparatus 10 from fraying.

Figure 3:
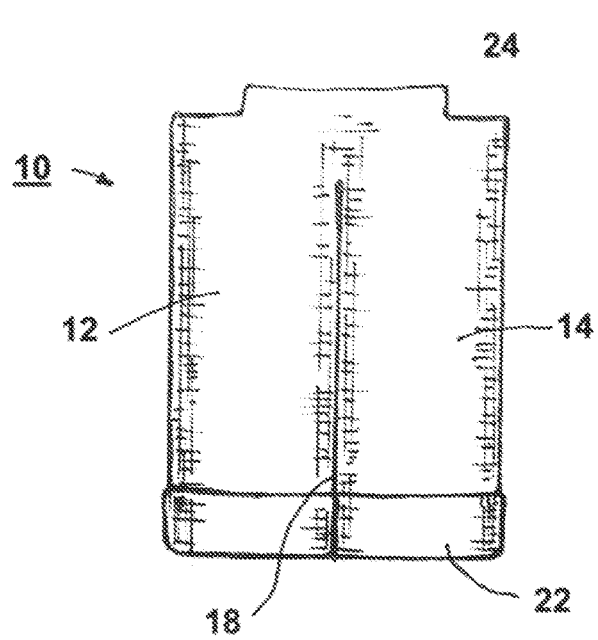
FIG. 3 is a diagrammatical top view of the finger sleeve apparatus of FIG. 1 in accordance with embodiments of the present invention.

FIG. 3 shows a top view of the finger sleeve support apparatus 10. As seen in the illustration, the row of stitching 18 denotes the region in which the first finger sleeve 12 is attached to the second finger sleeve 14. As described above, the hem overlay 22 is disposed at the first end of the finger sleeve support apparatus 10, and the tab 24 is disposed at the second end of the finger sleeve support apparatus 10.

Figure 5:
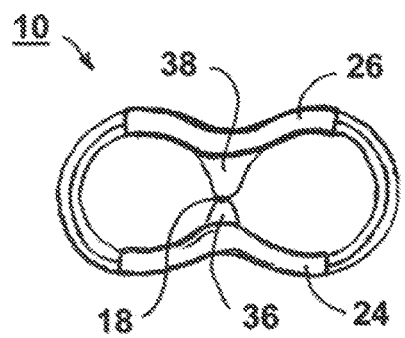
FIG. 5 is a second end view of the finger sleeve apparatus of FIG. 1 in accordance with embodiments of the present invention.
Figure 4:
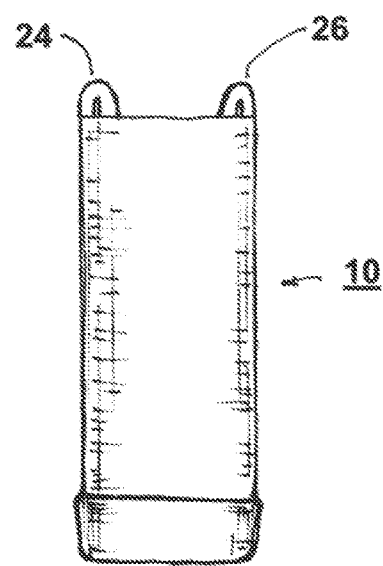
FIG. 4 is diagrammatical first end side view of the finger sleeve apparatus of FIG. 1 in accordance with embodiments of the present invention.

FIG. 4 is a side view of the finger sleeve support apparatus 10 showing that the tab 24 and the tab 26 may be formed by folding over the material of the finger sleeve support apparatus 10 to provide sufficient thickness to the tabs 24, 26 so as to enable grasping by the user. In an exemplary embodiment, terminal ends 36 and 38 of the respective tabs 24 and 26 may be secured in place by a portion of the row of stitching 18, as best seen in FIG. 5. The finger sleeve support apparatus 10 may include a lining (not shown) disposed inside the first finger sleeve 12 and the second finger sleeve 14 so as to enable the finger sleeve support apparatus 10 to be more easily slipped onto and off the fingers of the wearer.

The finger sleeve support apparatus 10 may be worn on the middle and ring fingers of a user, for example, with the tab 24 disposed near the knuckles and the overlay 22 near the finger tips, as shown in FIG. 6. In this case, the user's middle and ring fingers cannot move independently of each other, which further restricts the movement of other fingers, thereby protecting the user from an accidental injury of his fingers.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied alone or in some combination, to one or more of the other embodiments of the disclosure, whether or not such embodiments are described, and whether or not such features are presented as being a part of a described embodiment. Thus, the breadth and scope of the present disclosure should not be limited by any of the above-described exemplary embodiments.

What is claimed is:

1. A finger sleeve support apparatus, comprising:
a cylindrical member comprising a hem overlay on a first end and a protruding tab on a second end;
a row of stitching extending from the hem overlay to the protruding tab, in a center of the cylindrical member to form an adjoined structure, comprising of a middle finger sleeve adjoined to a ring finger sleeve, the middle finger sleeve configured to receive a middle finger of a wearer's hand and the ring finger sleeve configured to receive a ring finger of the wearer's hand, the protruding tab configured to be disposed at a major knuckle region and the hem overlay configured to be disposed at a fingertip region, of the middle finger and the ring finger, so as to restrain relative movement of the middle finger and the ring finger;
wherein the protruding tab is foldable by folding over a material of the finger sleeve support apparatus; and
wherein the protruding tab is secured by the row of stitching when the protruding tab is folded.

2. The finger sleeve support apparatus of claim 1, wherein the cylindrical member comprises a neoprene fabric.

3. The finger sleeve support apparatus of claim 1, wherein the hem overlay comprises a wear resistant fabric.

4. The finger sleeve support apparatus of claim 1, wherein the hem overlay comprises a first hem overlay disposed at a first end of the middle finger sleeve.

5. The finger sleeve support apparatus of claim 4, wherein the hem overlay further comprises a second hem overlay disposed at the first end of the ring finger sleeve.

6. The finger sleeve support apparatus of claim 5, wherein the protruding tab comprises a first tab disposed at a second end of the middle finger sleeve.

7. The finger sleeve support apparatus of claim 6, wherein the protruding tab further comprises a second tab disposed at the second end of the ring finger sleeve.

8. The finger sleeve support apparatus of claim 1, wherein the row of stitching extending from the hem overlay to the protruding tab, extends such that the protruding tab is equally disposed on the middle and ring finger sleeve.

9. The finger Sleeve support apparatus of claim 1, wherein the protruding tab is foldable such that a fold in the protruding tab is perpendicular to the row of stitching.

10. A finger sleeve support apparatus comprising:
a first cylindrical member with an internal lining and having a first opening;
a second cylindrical member with an internal lining, connected to the first cylindrical member via a line of stitching to form an adjoined structure and the second cylindrical member having a second opening;
a hem overlay disposed at a first end of the first and second cylindrical members,
a protruding member disposed at a second end of the first and second cylindrical members;
the line of stitching extending from the hem overlay to the protruding member;
wherein the first and second cylindrical members are configured to receive a middle finger and a ring finger of a wearer's hand respectively, the protruding member configured to be disposed at a major knuckle region and the hem overlay configured to be disposed at a fingertip region, of the middle finger and the ring finger, so as to restrain relative movement of the middle finger and the ring finger;
wherein the protruding member is foldable by folding over a material of the finger sleeve support apparatus; and wherein the protruding member is secured by the line of stitching when the protruding member is folded.

11. The finger sleeve support apparatus of claim 10, wherein the first and second cylindrical members comprise a neoprene fabric.

12. The finger sleeve support apparatus of claim 10, wherein the hem overlay comprises a wear-resistant fabric.

13. A finger sleeve support apparatus, consisting of:
   a cylindrical member comprising a hem overlay on a first end and a protruding tab on a second end;
   a row of stitching extending from the hem overlay to the protruding tab, in a center of the cylindrical member to form an adjoined structure, comprising of a middle finger sleeve adjoined to a ring finger sleeve, the middle finger sleeve configured to receive a middle finger of a wearer's hand and the ring finger sleeve configured to receive a ring finger of the wearer's hand, the protruding tab configured to be disposed at a major knuckle region and the hem overlay configured to be disposed at a fingertip region, of the middle finger and the ring finger, so as to restrain relative movement of the middle finger and the ring finger;
   wherein the protruding tab is foldable by folding over a material of the finger sleeve support apparatus; and
   wherein the protruding tab is secured by the row of stitching when the protruding tab is folded.

14. The finger sleeve support apparatus of claim 13, wherein the cylindrical member comprises a neoprene fabric.

15. The finger sleeve support apparatus of claim 13, wherein the hem overlay comprises a wear resistant fabric.

16. The finger sleeve support apparatus of claim 13, wherein the hem overlay consists of a first hem overlay disposed at a first end of the middle finger sleeve and a second hem overlay disposed at the first end of the ring finger sleeve.

17. The finger sleeve support apparatus of claim 16, wherein the protruding tab consists of a first tab disposed at a second end of the middle finger sleeve and a second tab disposed at the second end of the ring finger sleeve.

* * * * *